United States Patent [19]

Hydes et al.

[11] 4,394,319

[45] Jul. 19, 1983

[54] CO-ORDINATION COMPOUND OF PLATINUM

[75] Inventors: Paul C. Hydes; Derek R. Hepburn, both of Reading, England

[73] Assignee: Johnson Matthey Public Limited Company, London, England

[21] Appl. No.: 296,478

[22] Filed: Aug. 26, 1981

[30] Foreign Application Priority Data

Sep. 3, 1980 [GB] United Kingdom ............... 8028484
May 20, 1981 [GB] United Kingdom ............... 8115549

[51] Int. Cl.$^3$ ............................................. C07F 15/00
[52] U.S. Cl. ................................. 260/429 R; 424/287
[58] Field of Search ................................. 260/429 R

[56] References Cited

U.S. PATENT DOCUMENTS 4,119,654 10/1978 Tobe et al. ................. 260/429 R
4,228,090 10/1980 Hydes et al. ................. 260/429 R

OTHER PUBLICATIONS

Tobe et al., J. of Clinical Hematology and Oncology, vol. 7, No. 1, pp. 129 to 131 & 133, (1977).

*Primary Examiner*—Helen M. S. Sneed
*Attorney, Agent, or Firm*—Cushman, Darby & Cushman

[57] ABSTRACT

The compound

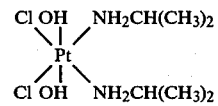

useful for the chemotherapeutic treatment of cancer or malignant neoplasms is provided in substantially pure form by a method of preparation involving a novel intermediate adduct with dimethylacetamide.

3 Claims, 9 Drawing Figures

CO-ORDINATION COMPOUND OF PLATINUM

This invention relates to compositions of matter containing platinum, and more particularly to such compositions which are useful for the chemotherapeutic treatment of cancer or malignant neoplasms.

Our British Pat. No. 1,578,323 describes and claims a composition of matter comprising a co-ordination compound of platinum having the structure:

in which X and Y are halogenoid groups which are the same or different and are preferably both chloride but may be other halide or pseudohalide such as cyanate, thiocyanate and azide and A and B are the same or different branched chain aliphatic amine groups co-ordinated to the Pt through their N atoms.

Also described and claimed in the said British patent is a composition for the treatment of cancer or a malignant neoplasm comprising a co-ordination compound of platinum having the structure:

in which X and Y are halogenoid groups which are the same or different and are preferably both chloride but may be other halide or pseudohalide such as cyanide, cyanate, thiocyanate, or azide or other similar groups and A and B are the same or different branched chain aliphatic amine groups or C-substituted branched chain aliphatic amine groups co-ordinated to the Pt through their N atoms each having the general formula $$C_nR_{2n+1}NH_2$$

in which n may vary from 3 to 9 and in which all of the R groups are either the same or different and are preferably all hydrogen but may be selected from the group consisting of hydrogen, alkyl, aryl, alkaryl, aralkyl, halogen, pseudohalogen, hydroxy, carbonyl, formyl, nitro, amido, amino, sulphonic acid, sulphonic acid salt, carboxylic acid, carboxylic acid salt, and substituted alkyl, aryl, alkaryl and aralkyl groups.

The platinum is preferably present at $Pt^{4+}$, thus producing a neutral complex with two hydroxyl and two halide ligands.

Although R groups other than hydrogen are not normally preferred, they may be used and may comprise lower alkyl such as methyl or ethyl or a solubilizing group such as a sulphonic acid group. Solubilizing groups, such as carboxylic acid, sulphonic acid, and salts thereof, for example the sodium, potassium or lithium salts, are sometimes appropriate as substituents when the clinical conditions require high solubility.

Throughout the specification and claims of the said British patent, the term "halogenoid" is used to mean  halide (chloride, bromide, iodide or fluoride) or pseudohalide such as cyanide, cyanate, thiocyanate or azide.

Suitable branched chain amine compounds which may be used for groups A and B are said to be isopropylamine, isobutylamine, isoamylamine and 2-aminohexane.

One particular compound falling within the scope of the claims of GB No. 1,578,323 is where A and B in the general formula are both isopropylamine and X and Y are both chloride, the complex thus being cis-dichloro-trans-dihydroxy-bis(isopropylamine)platinum(IV). The method of preparation quoted in the specification of the said patent comprises heating a slurry of the corresponding cis-diaminedichloroplatinum(II) complex with hydrogen peroxide solution, boiling for 0.5 hours until yellow in colour, chilling, filtering, washing the residue with water and ether and drying in air. The resulting crude product is recrystallised from a water/hydrogen peroxide solvent mixture and dried in vacuo. From the elemental analysis figures, the infra-red absorption spectrum and X-ray crystallography of a single crystal, the formula of the corresponding 1:1 hydrate was assigned to it.

Subsequent work has shown that the complex as prepared and recrystallised as described above in fact exists as an adduct with hydrogen peroxide in a ratio of 2 molecules complex to 1 molecule $H_2O_2$, but the presence of hydrogen peroxide is considered disadvantageous from the pharmaceutical viewpoint. However, attempts to remove it by physical means have invariably failed due to decomposition of the complex involving loss of the hydroxy ligands. It has hitherto been considered, therefore, that it is impossible to prepare and isolate the complex in substantially pure form, that is, devoid of detectable amounts of hydrogen peroxide or other solvating molecules.

We have now found that the complex may after all be prepared in substantially pure form.

According to the invention, therefore, we provide a co-ordination compound of platinum in substantially pure form and having the structure The compound according to the present invention is useful for the chemotherapeutic treatment of cancer or malignant neoplasms.

The invention also includes a process for the preparation of a co-ordination compound of platinum in substantially pure form and having the structure the process comprising reacting cis-dichloro-di(isopropylamine)platinum(II) with hydrogen peroxide, isolating the product, dissolving the said product in N,N-dimethylacetamide, isolating the resulting product which comprises a 1:1 adduct of the said compound with N,N-dimethylacetamide, and thereafter removing the said N,N-dimethylacetamide under vacuum at a temperature less than 80° C., preferably less than 50° C.

We have found that the use of dimethylacetamide in the process according to the invention to provide the intermediate 1:1 adduct is successful in removing hydrogen peroxide where straightforward recrystallisations using general purpose solvents have failed. As indicated above, water is unsuccessful; so too is methanol, despite the vast numerical excess of solvent molecules over hydrogen peroxide molecules, whereas it would have been expected that either of these solvents would have been suitable, due to their polarity and their miscibility with hydrogen peroxide.

The intermediate 1:1 adduct of cis-dichloro-trans-dihydroxy-bis(isopropylamine)platinum(IV) with dimethylacetamide is itself a novel composition of matter which is isoltable, stable and characterisable.

Embodiments of the invention will now be described with reference to the following preparative example, which refers (a) to the preparation of crude cis-dichloro-trans-dihydroxy-bis(isopropylamine)Pt(IV) and (b) to the preparation of the intermediate adduct with dimethylacetamide with subsequent isolation of the substantially pure product.

EXAMPLE (A) Preparation of crude product

Recrystallised cis-Pt(i-$C_3H_7NH_2)_2Cl_2$ (26.8 g) was slurried in hot water (50 ml) and aqueous hydrogen peroxide (100 vols; 100 ml) was added with stirring. The slurry was boiled for half an hour until yellow in colour and was then chilled and filtered. The residue was washed with water, then with ether and was then dried in air. The yield was 10.5 g (35%).

Elemental analysis figures were as follows:

|  | C | H | N | O | Cl |
|---|---|---|---|---|---|
| Calculated % | 16.55 | 4.87 | 6.43 | 11.03 | 16.28 |
| Found % | 16.59 | 4.90 | 6.48 | 10.80 | 16.20 |

The IR hydrozyl stretching absorption ($\gamma$ C—H) occurs at 3515 cm$^{-1}$.

(b) Preparation of the adduct and isolation of substantially pure product

The crude product (11 g) prepared as above was dissolved in N,N-dimethylacetamide (approx 1 l) and the solution was filtered through a glass sinter (porosity 4) to remove any insoluble material present. The solution was then cooled to 5° C. for 2 hours, seeded to prevent super-saturation and stored at −10° C. for several days. The resulting crystals were filtered off, washed with ether and dried.

Removal of N,N-dimethylacetamide to yield substantially pure product was carried out by heating the crystals to a temperature of 50° C. or less at a pressure of 0.1 torr for several days, or until the absence of N,N-dimethylacetamide was confirmed by thermal gravimetric analysis and/or gas liquid chromatography.

The step of dissolving the crude product from (a) above in N,N-dimethylacetamide may be carried out at ambient temperatures but we prefer to use a slightly elevated temperature, that is, not higher than about 40° C.

Further optional purification steps include recrystallisation of the crude product (step (a) above) from dilute hydrogen peroxide solution, followed by drying at approximately 50° C. in vacuo, and further filtering the N,N-dimethylacetamide solution (step (b) above) through a silica gel bed (70-230 mesh) to remove any polyhydroxy platinum species.

Analytical data for characterisation of the prior art hydrogen peroxide adduct, the compound according to the invention and the N,N-dimethylacetamide adduct are as described below and as illustrated in the accompanying drawings of which.

Figure 1:
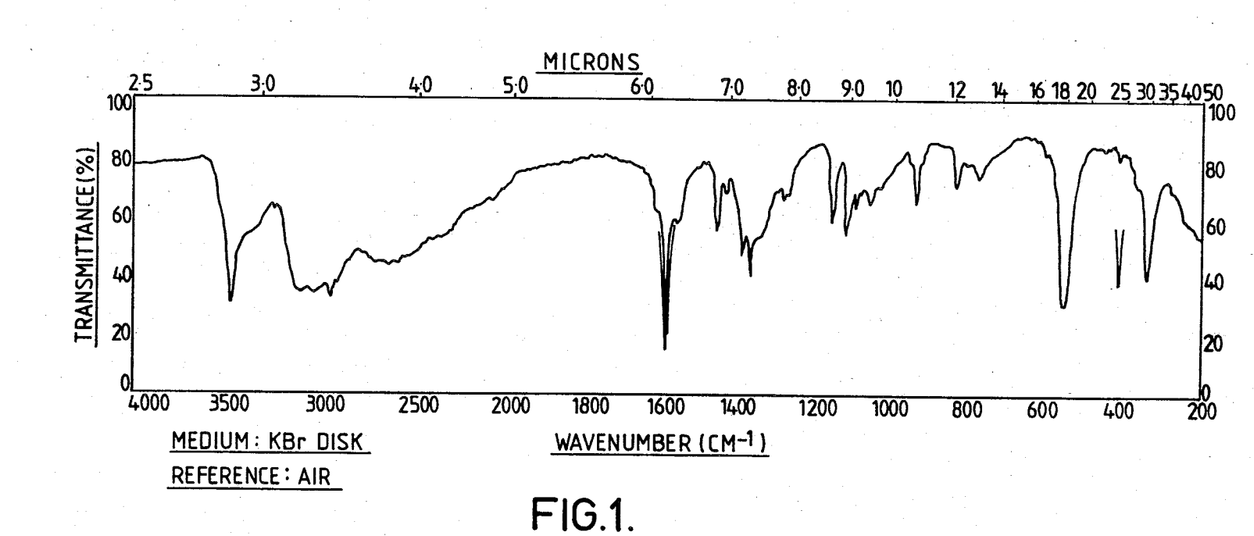
FIG. 1 is an IR spectrum of the prior art hydrogen peroxide adduct.
Figure 2:
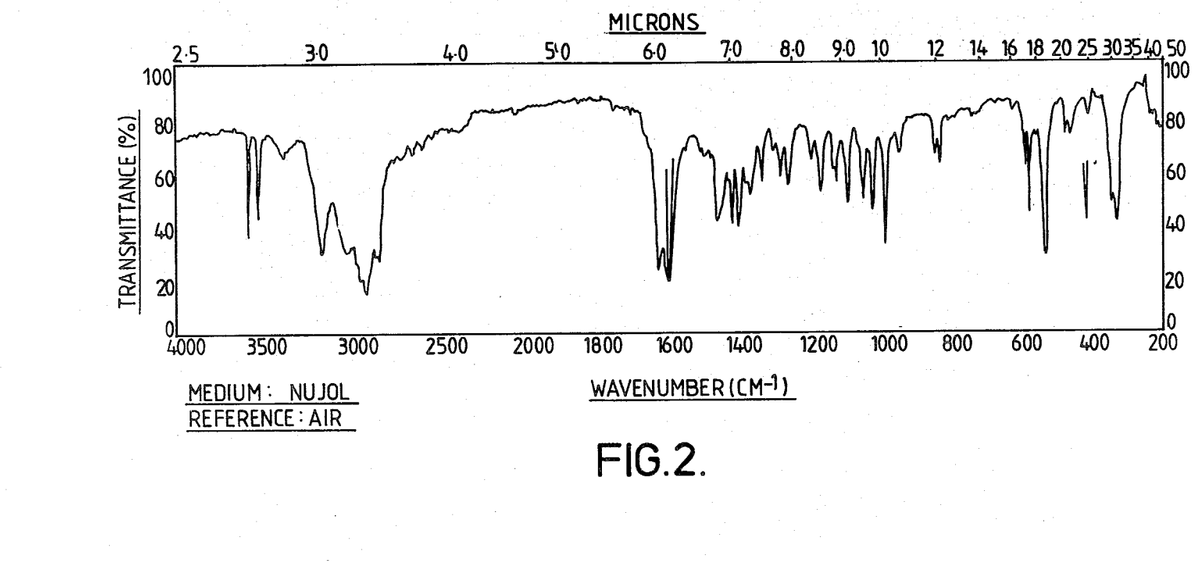
FIG. 2 is an IR spectrum of the novel dimethylacetamide adduct.
Figure 3:
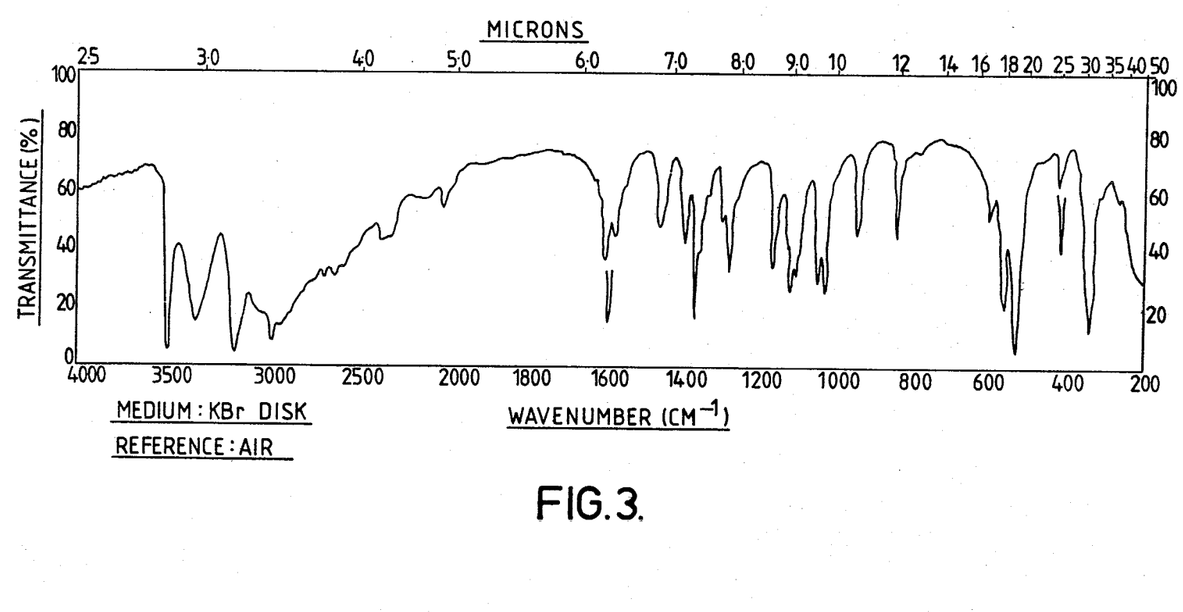
FIG. 3 is an IR spectrum of the compound according to the invention.

In the details which follow, cis,trans,cis-[$PtCl_2(OH)_2(iPrNH_2)_2$]—the compound according to the invention—was prepared as individual batches A, B, C which were then thoroughly mixed together to give composite batch X. Analytical data was as follows:

| Physical form: | Yellow powder (all batches) | | | | | |
|---|---|---|---|---|---|---|
| Infrared spectrum: | See FIGS. 1-3 | | | | | |
| Elemental analysis: | Batch | C (%) | H (%) | N (%) | O (%) | Cl (%) | Pt (%) |
| | A | 17.27 | 4.84 | 6.79 | 8.20 | 16.58 | 46.43 |
| | B | 17.26 | 4.87 | 6.76 | 7.88 | 16.85 | 46.47 |
| | C | 17.17 | 4.80 | 6.76 | 7.80 | 16.86 | 46.45 |
| | X | 17.13 | 4.81 | 6.71 | 7.75 | 16.81 | 46.45 |
| | Theory | 17.23 | 4.82 | 6.70 | 7.65 | 16.95 | 46.65 |
| HPLC (bulk assay): | % purity Batch | | | | | |
| | A | 97.31 | | | | |
| | B | 100.17 | | | | |
| | C | 97.63 | | | | |
| | X | 98.27 | | | | |
| Impurity levels: | Batch | Wt. % Peroxide value | DMA | | | |
| | A | 0.05 | <0.06 | | | |
| | B | 0.03 | <0.09 | | | |
| | C | 0.05 | 0.15 | | | |
| | X | 0.06 | 0.024 | | | |
| Moisture content: | <0.25 wt % (all batches) by TGA. | | | | | |

Figure 4:
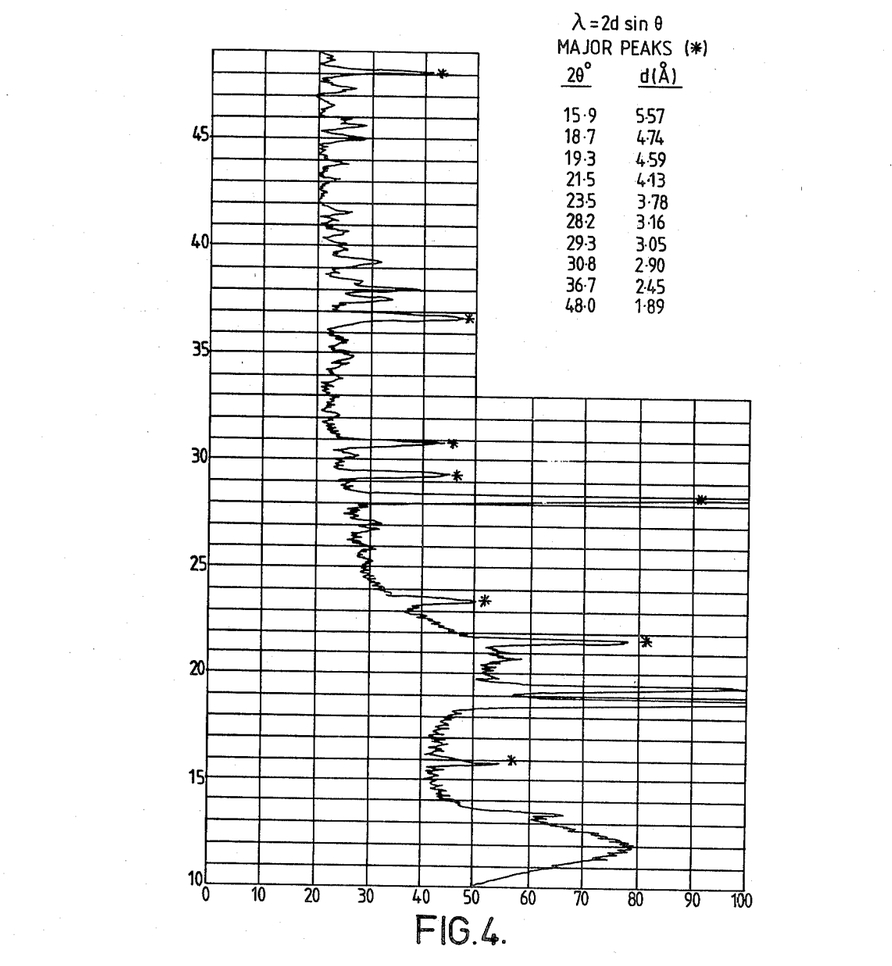
FIG. 4 is an X-ray powder diffraction pattern of the prior art hydrogen peroxide adduct.
Figure 5:
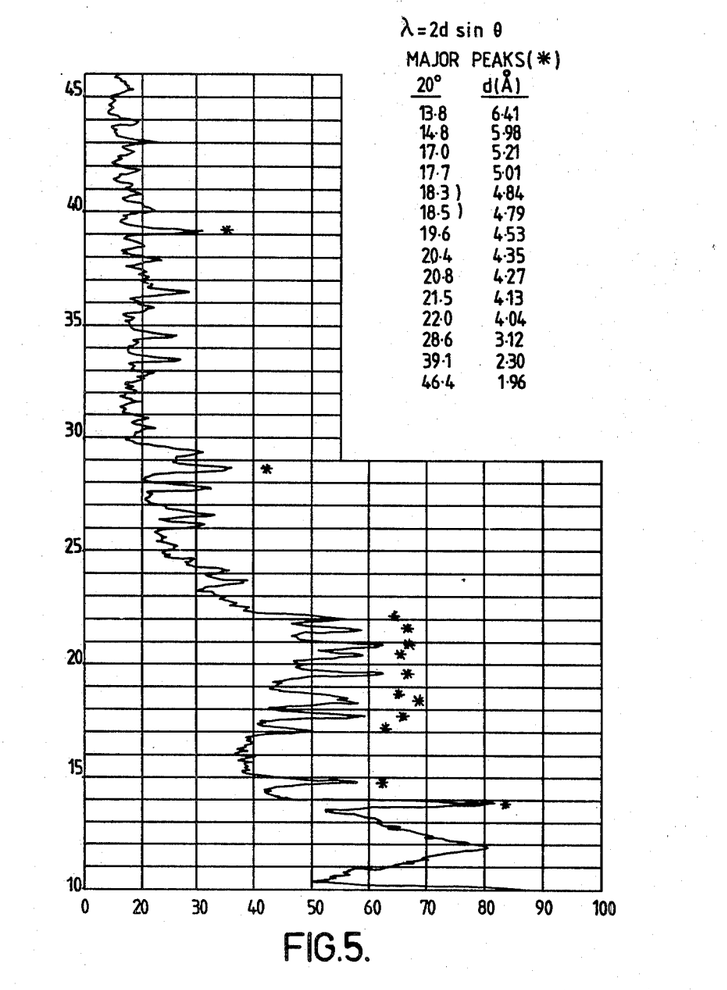
FIG. 5 is an X-ray powder diffraction pattern of the novel N,N-dimethylacetamide adduct.
Figure 6:
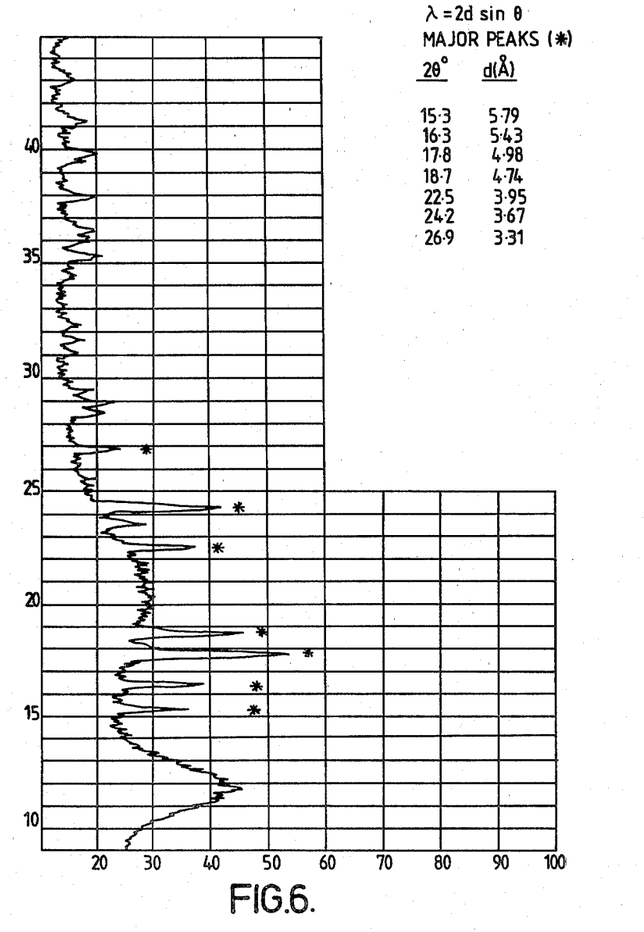
FIG. 6 is an X-ray powder diffraction pattern of the compound according to the invention.

Referring now the drawings, FIGS. 1, 2 and 3 show infrared spectra of various compounds, the most notable feature being the different absorption patterns for OH stretch in the region of 3500 cm$^{-1}$, indicating that the prior art hydrogen peroxide adduct, the novel N,N-dimethylacetamide adduct and the compound according to the invention in substantially pure form are all separately isolable and characterisable compounds. FIGS. 4, 5 and 6 are indicative of the same conclusion, the evidence in this case being the X-ray powder diffraction patterns. On each figure the $2\theta$ angle is given and also the separation of the planes in Å.

Figure 7:
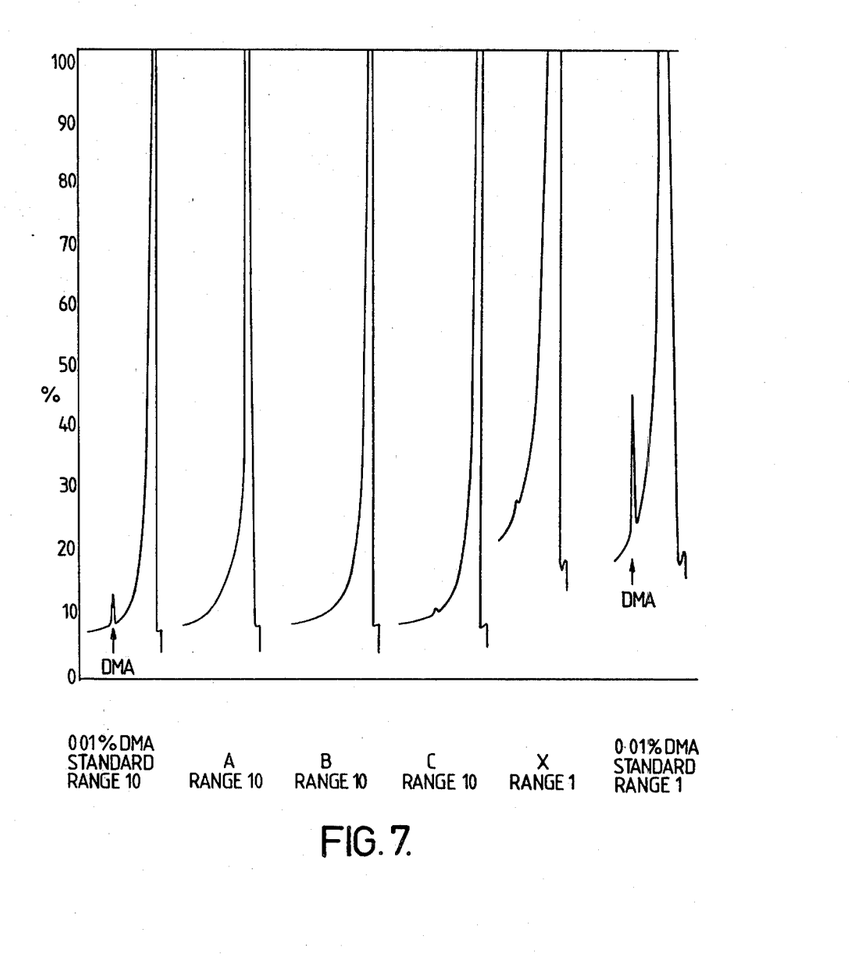
FIG. 7 shows chromatograms of various compounds.

FIG. 7 shows the amounts of N,N-dimethylacetamide (DMA) present in batches A, B, C and X as measured by gas liquid chromatography.

For a given range, a similar response in A, B, C or X compared with the standard would represent a DMA concentration of ca. 1% by weight.

Figure 8:
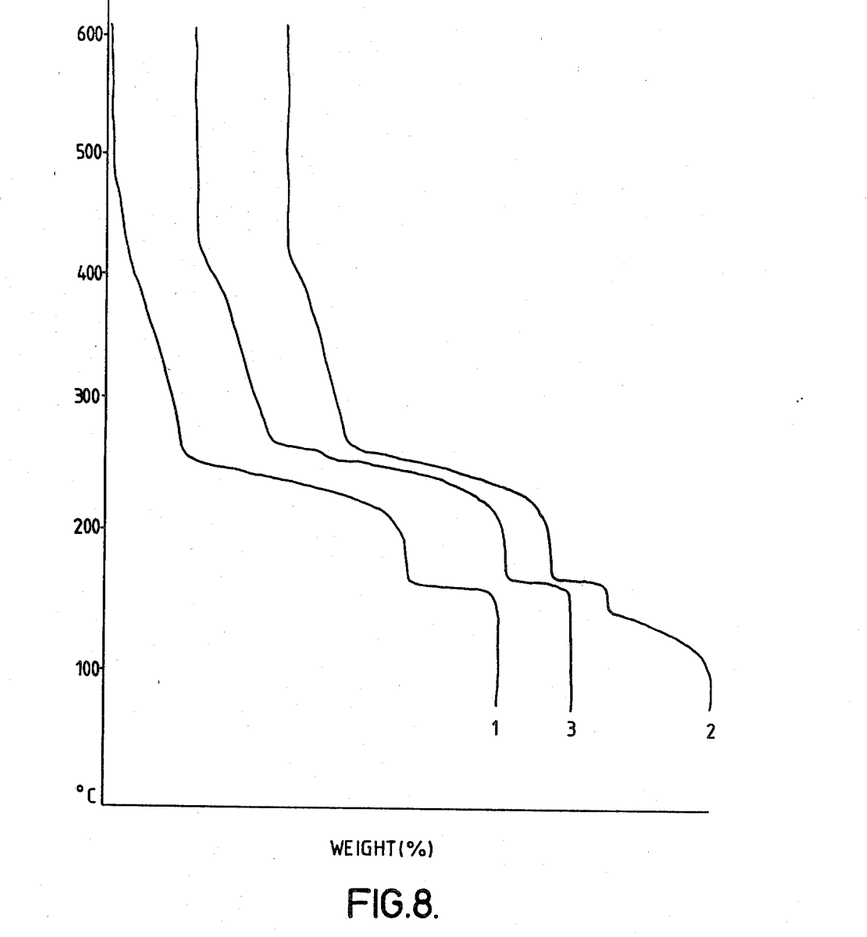
FIG. 8 shows the results of thermal gravimetric analysis of various compounds.

Referring to FIG. 8, which shows the results of thermal gravimetric analysis of various compounds, the legend is as follows:

Line 1 represents a prior art hydrogen peroxide adduct compound;
Line 2 represents a novel N,N-dimethylacetamide adduct compound;
Line 3 represents a compound according to the invention.

The traces have been abitrarily displaced on the "weight (%)" axis for ease of presentation.

It is seen that line 1 indicates a greater weight loss at about 160° C. due to loss of trans OH groups as well as $H_2O_2$, whereas lines 2 and 3 show substantially the same weight loss at that temperature due to the loss of the trans OH groups alone. In line 2, the sloping shoulder up to the temperature of about 150° C. represents loss of N,N-dimethylacetamide and thereafter the compounds represented by lines 2 and 3 are seen to be substantially identical.

Figure 9:
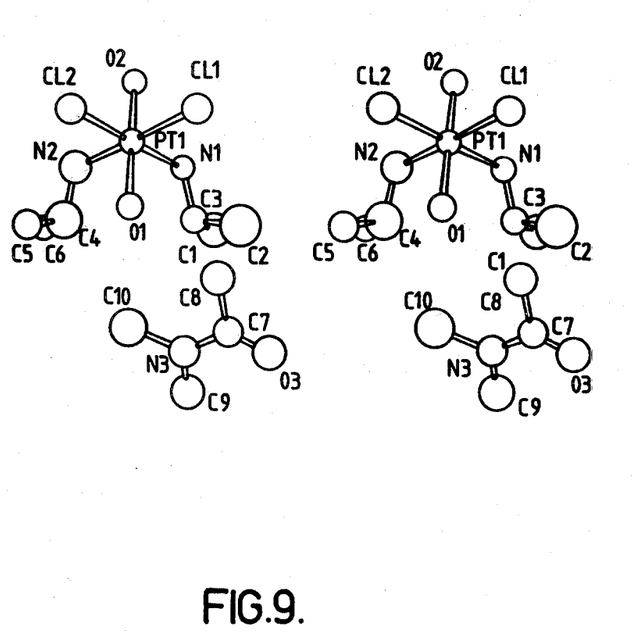
FIG. 9 is a stereoscopic view of the N,N-dimethylacetamide adduct.

Referring to FIG. 9, the stereoscopic view shown was derived by X-ray crystallographic study of a single crystal of the N,N-dimethylacetamide adduct. Attempts to isolate a single crystal of the substantially pure compound according to the invention from a single crystal of the N,N-dimethylacetamide adduct resulted in an agglomeration of microcrystallites, the X-ray powder pattern for which is shown in FIG. 6.

The substantially pure cis-dichloro-trans-dihydroxy-bis(isopropylamine)Pt(IV) may be administered in substantially the same manner as described in GB No. 1,578,323 with respect to the prior are hydrogen peroxide adduct.

We claim:

1. A process for the preparation of a co-ordination compound of platinum in substantially pure form and having the structure comprising reacting cis-dichloro-di(isopropylamine)-platinum(II) with hydrogen peroxide, isolating the product, dissolving the said product in N,N-dimethylacetamide, isolating the resulting product which comprises a 1:1 adduct of the said compound with N,N-dimethylacetamide and thereafter removing the said N,N-dimethylacetamide under vacuum at a temperature less than 80° C.

2. A process according to claim 1 in which the N,N-dimethylacetamide is removed under vacuum at a temperature less than 50° C.

3. A composition of matter comprising a 1:1 adduct of cis-dichloro-trans-dihydroxy-bis(isopropylamine)-platinum(IV) with dimethylacetamide.

* * * * *